(12) United States Patent
Mueller

(10) Patent No.: US 8,568,390 B2
(45) Date of Patent: Oct. 29, 2013

(54) ARTICULATING SURGICAL APPARATUS

(75) Inventor: Peter M. Mueller, Frederick, CO (US)

(73) Assignee: Covidien LP, Mansfield, MA (US)

(*) Notice: Subject to any disclaimer, the term of this patent is extended or adjusted under 35 U.S.C. 154(b) by 281 days.

(21) Appl. No.: 13/186,673

(22) Filed: Jul. 20, 2011

(65) Prior Publication Data

US 2013/0023924 A1  Jan. 24, 2013

(51) Int. Cl.
*A61B 17/00* (2006.01)

(52) U.S. Cl.
USPC ............... 606/1; 606/205; 606/113; 600/104; 600/137; 227/176.1

(58) Field of Classification Search
USPC .............. 606/205, 1, 113, 110, 130; 600/137, 600/104; 605/110, 113; 227/176.1, 19, 227/179.1, 178.1
See application file for complete search history.

(56) References Cited

U.S. PATENT DOCUMENTS

| | | | |
|---|---|---|---|
| 3,306,634 A | 2/1967 | Groves et al. | |
| 5,374,277 A | 12/1994 | Hassler | |
| 5,417,203 A | 5/1995 | Tovey et al. | |
| 5,476,479 A | 12/1995 | Green et al. | |
| 5,483,952 A | 1/1996 | Aranyi | |
| 5,501,654 A | 3/1996 | Failla et al. | |
| 5,601,572 A | 2/1997 | Middleman et al. | |
| 5,609,601 A | 3/1997 | Kolesa et al. | |
| 5,673,840 A | 10/1997 | Schulze et al. | |
| 5,704,534 A | 1/1998 | Huitema et al. | |
| 5,762,067 A | 6/1998 | Dunham et al. | |
| 5,820,009 A | 10/1998 | Melling et al. | |
| 5,823,066 A | 10/1998 | Huitema et al. | |
| 5,855,311 A * | 1/1999 | Hamblin et al. | ........... 227/176.1 |
| 5,860,995 A | 1/1999 | Berkelaar | |
| 5,904,667 A | 5/1999 | Falwell | |
| 6,063,098 A | 5/2000 | Houser et al. | |
| 6,083,234 A | 7/2000 | Nicholas et al. | |
| 6,352,539 B1 * | 3/2002 | Avellanet | ....................... 606/113 |
| 7,533,906 B2 | 5/2009 | Luettgen et al. | |
| 7,588,176 B2 | 9/2009 | Timm et al. | |
| 7,588,546 B2 | 9/2009 | de Andrade | |
| 7,588,575 B2 | 9/2009 | Colleran et al. | |
| 7,608,081 B2 | 10/2009 | Abdelgany | |
| 7,615,067 B2 | 11/2009 | Lee et al. | |
| 7,618,442 B2 | 11/2009 | Spitler et al. | |
| 7,637,410 B2 | 12/2009 | Marczyk | |
| 7,670,334 B2 | 3/2010 | Hueil et al. | |
| 7,789,283 B2 | 9/2010 | Shah | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,824,411 B2 | 11/2010 | Varieur et al. | |
| 7,824,413 B2 | 11/2010 | Varieur et al. | |

(Continued)

*Primary Examiner* — Aaron Roane
*Assistant Examiner* — Victor Shapiro

(57) ABSTRACT

An endoscopic instrument includes a housing having shaft. The shaft includes an articulating section disposed thereon. An end effector assembly operatively connects to a distal end of the shaft and is configured to treat tissue. A plurality of tendons operably couples to the articulating section and is translatable along a longitudinal axis to effect articulation of the shaft about the articulating section. Each of the tendons includes a respective locking ferrule disposed thereon. A locking catheter is disposed within the shaft and between the plurality of tendons to selectively engage each respective locking ferrule. The locking catheter is rotatable within the shaft from a first position to allow articulation of the shaft about the articulating section, to a second position to prevent articulation of the shaft.

16 Claims, 22 Drawing Sheets

(56) References Cited

U.S. PATENT DOCUMENTS

| | | |
|---|---|---|
| 7,832,612 B2 | 11/2010 | Baxter, III et al. |
| 7,837,080 B2 | 11/2010 | Schwemberger |
| 7,842,044 B2 | 11/2010 | Runco et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,887,539 B2 | 2/2011 | Dunbar, Jr. et al. |
| 7,887,541 B2 | 2/2011 | Runco et al. |
| 7,905,380 B2 | 3/2011 | Shelton, IV et al. |
| 7,905,381 B2 | 3/2011 | Baxyet, III et al. |
| 7,905,907 B2 | 3/2011 | Spitler et al. |
| 7,922,061 B2 | 4/2011 | Shelton, IV et al. |
| 7,931,677 B2 | 4/2011 | Abdelgany |
| 7,934,630 B2 | 5/2011 | Shelton, Iv et al. |
| 2003/0036748 A1* | 2/2003 | Cooper et al. .................... 606/1 |
| 2005/0149048 A1 | 7/2005 | Leport et al. |
| 2006/0178556 A1 | 8/2006 | Hasser et al. |
| 2007/0027468 A1 | 2/2007 | Wales et al. |
| 2007/0219550 A1 | 9/2007 | Thompson et al. |
| 2007/0221701 A1 | 9/2007 | Ortiz et al. |
| 2007/0225562 A1 | 9/2007 | Spivey et al. |
| 2008/0039776 A1 | 2/2008 | Ghabrial et al. |
| 2008/0255420 A1* | 10/2008 | Lee et al. ...................... 600/137 |
| 2009/0023986 A1 | 1/2009 | Stewart et al. |
| 2009/0065549 A1 | 3/2009 | Viola |
| 2009/0088792 A1 | 4/2009 | Hoell, Jr. et al. |
| 2009/0125019 A1 | 5/2009 | Douglass et al. |
| 2009/0137984 A1 | 5/2009 | Minnelli |
| 2010/0030018 A1 | 2/2010 | Fortier et al. |
| 2010/0057121 A1 | 3/2010 | Piskun et al. |
| 2010/0168510 A1* | 7/2010 | Rogers et al. ................. 600/104 |
| 2010/0179540 A1 | 7/2010 | Marczyk et al. |
| 2010/0298638 A1 | 11/2010 | Slater |
| 2010/0298854 A1 | 11/2010 | Slater |

* cited by examiner

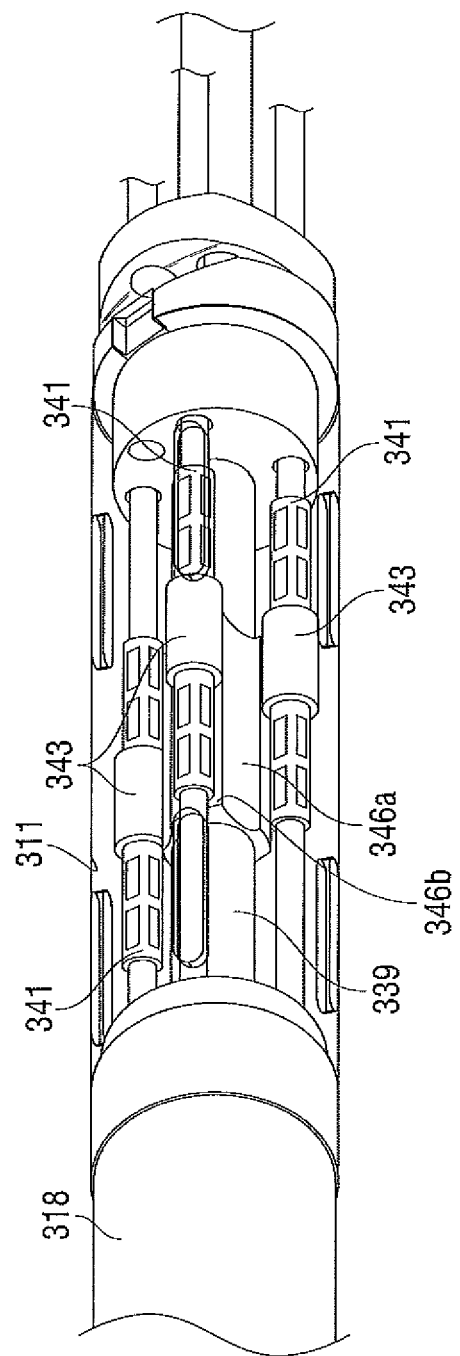

ARTICULATING SURGICAL APPARATUS

BACKGROUND

1. Technical Field

The present disclosure relates to an articulating surgical apparatus. More particularly, the present disclosure relates to an articulating surgical apparatus including a locking device configured to lock the surgical apparatus in a non-articulated configuration.

2. Description of Related Art

Surgical instruments that are configured to articulate or bend are well known in the medical arts. Surgical instruments of this nature are utilized in many surgical procedures. For example, laparoscopic, endoscopic, or other minimally invasive surgical procedures are just a few of the many surgical procedures where articulating surgical instruments may find use. When utilized in such procedures, the surgical instruments may include a housing, a handle assembly, an articulating shaft, a device for articulating the shaft, and an end effector including a pair of jaw members.

As can be appreciated, the relatively small operable working space that is created within a cavity of a patient during a surgical procedure often makes it difficult for the surgeon to position the jaw members adjacent or close to target tissue. The articulating shaft allows a surgeon to position the jaw members adjacent target tissue.

Various articulating devices or mechanisms may be utilized to articulate the shaft. For example, some surgical instruments utilize one or more articulating cables or tendons that couple to one or more articulation links on the shaft. Typically, the cables or tendons provide a mechanical interface from the one or more articulation links to an actuation device, e.g., rotatable dials, disposed on the housing and/or handle assembly of the surgical instrument such that actuation of the actuation device moves or articulates the shaft about the articulation links. In particular, the cables or tendons are "pulled" or otherwise manipulated via one or more mechanisms in the handle assembly or the housing to articulate the shaft about the articulating links.

Under certain surgical scenarios, it may prove advantageous to maintain the shaft in a relatively fixed or stationary position, such as, for example, when positioning tissue between the jaw members or when the shaft is inserted through a trocar or cannula. Locking the cables or tendons so that the shaft is prevented from articulating typically requires eliminating, what is commonly referred to in the art as, cable or tendon "stretch" from the cables or tendons. Cable or tendon "stretch" is the ability of the cable or tendon to stretch under a predetermined load. To remove this cable or tendon stretch, the cables or tendons are typically highly loaded in tension. Removing this cable or tendon stretch limits and/or eliminates "post lock" articulation. However, due to the length of the surgical instrument and, thus, the corresponding length of the cables or tendons between the articulating links and the actuation device and/or locking device, a fairly large "spring rate" exists with a corresponding "stiffness" penalty being observed. That is, overtime, subjecting the cables or tendons to high load tension reduces the stiffness of the cables or tendons and, thus, the overall stiffness of the shaft. As can be appreciated, reducing the "stiffness" of the shaft may result in the shaft not functioning in a manner as intended.

SUMMARY

The present disclosure provides an endoscopic instrument. The endoscopic instrument includes a housing having shaft extending therefrom that defines a longitudinal axis therethrough. The shaft includes an articulating section disposed thereon. An end effector assembly operatively connects to a distal end of the shaft to treat tissue. In embodiments, the end effector includes a pair of first and second jaw members. wherein one or both of the first and second jaw members is movable relative to other jaw member from an open position, wherein the first and second jaw members are disposed in spaced relation relative to one another, to a clamping position, wherein the first and second jaw members cooperate to grasp tissue therebetween. A plurality of tendons operably couples to the articulating section and is translatable along the longitudinal axis to effect articulation of the shaft about the articulating section thereof. Each of the tendons includes a respective locking ferrule disposed thereon. A generally elongated locking catheter disposed within the shaft and between the plurality of tendons is configured to selectively engage each respective locking ferrule. The locking catheter is rotatable within the shaft from a first position, wherein the locking catheter is disengaged from the locking ferrules to allow axial movement of the plurality of tendons along the longitudinal axis to articulate the shaft, to a second position, wherein the locking catheter is engaged with the locking ferrules to prevent axial movement of the plurality of tendons along the longitudinal axis and prevent further articulation of the shaft.

The present disclosure provides an endoscopic instrument. The endoscopic instrument includes a housing having shaft extending therefrom that defines a longitudinal axis therethrough. The shaft includes an articulating section disposed thereon. An end effector assembly operatively connects to a distal end of the shaft to treat tissue. In embodiments, the end effector includes a pair of first and second jaw members. wherein one or both of the first and second jaw members is movable relative to other jaw member from an open position, wherein the first and second jaw members are disposed in spaced relation relative to one another, to a clamping position, wherein the first and second jaw members cooperate to grasp tissue therebetween. A plurality of tendons operably couples to the articulating section and is translatable along the longitudinal axis to effect articulation of the shaft about the articulating section thereof. Each of the tendons includes a respective locking ferrule disposed thereon. A generally elongated locking catheter disposed within the shaft and between the plurality of tendons is configured to selectively engage each respective locking ferrule. The locking catheter is rotatable within the shaft from a disengaged position to allow articulation of the shaft, to an engaged position, wherein the locking catheter cams each of the locking ferrules against the inner wall of the shaft creating a frictional interference therebetween to prevent axially movement thereof along the longitudinal axis and prevent further articulation of the shaft.

BRIEF DESCRIPTION OF THE DRAWING

Various embodiments of the present disclosure are described hereinbelow with references to the drawings, wherein:

FIGS. 6A-6D are partial cut-away views of a shaft illustrating a locking catheter and locking ferrules in various locked and an unlocked configurations according to yet another embodiment of the present disclosure.

DETAILED DESCRIPTION

Figure 1:
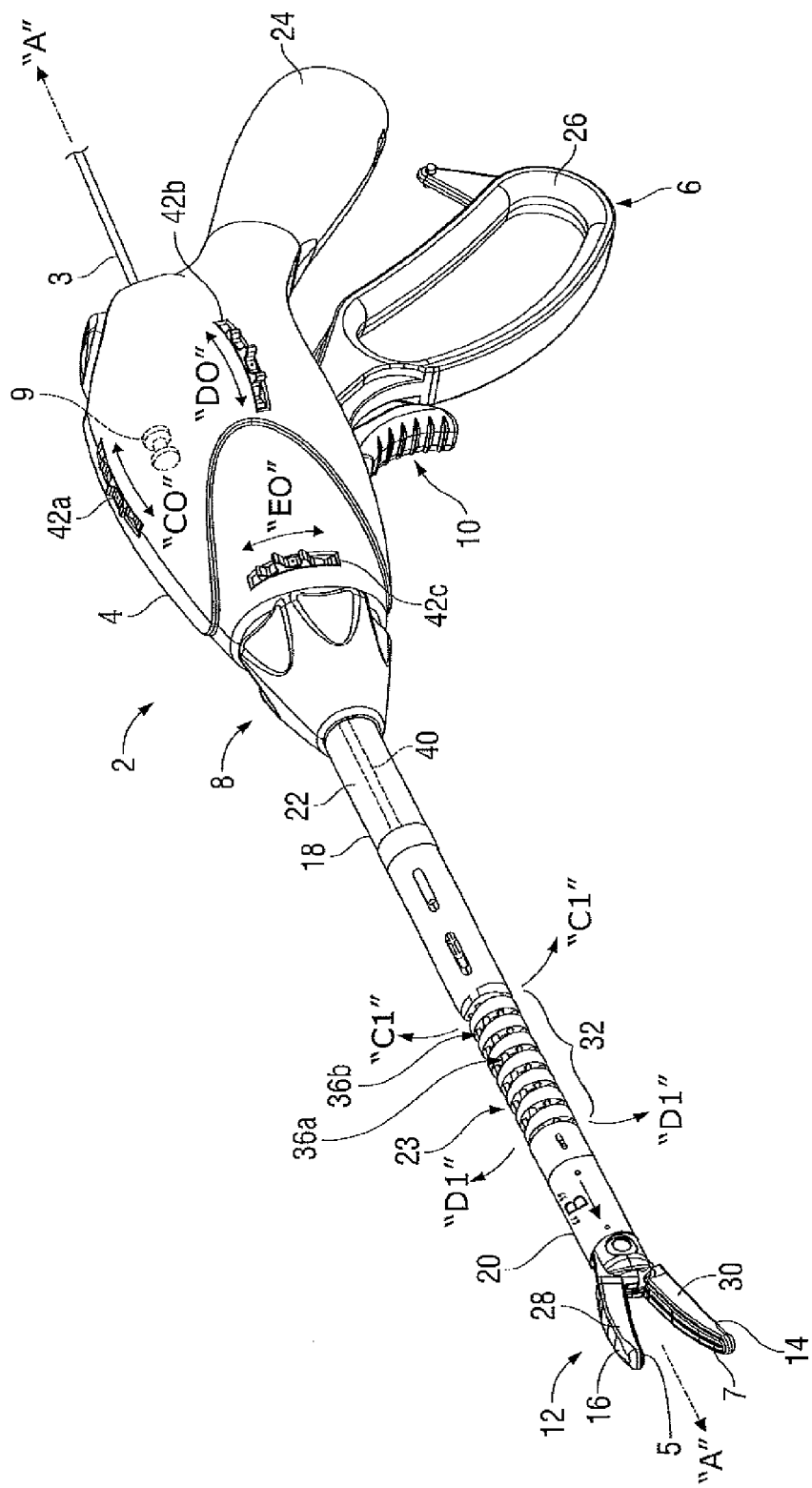
FIG. 1 is a side, perspective view of an endoscopic instrument including a shaft in an non-articulated configuration according to an embodiment of the present disclosure.

Detailed embodiments of the present disclosure are disclosed herein; however, the disclosed embodiments are merely examples of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, will refer to the end of a surgical instrument that is closer to the user, while the term "distal" will refer to the end of the surgical instrument that is farther from the user.

Figure 2:
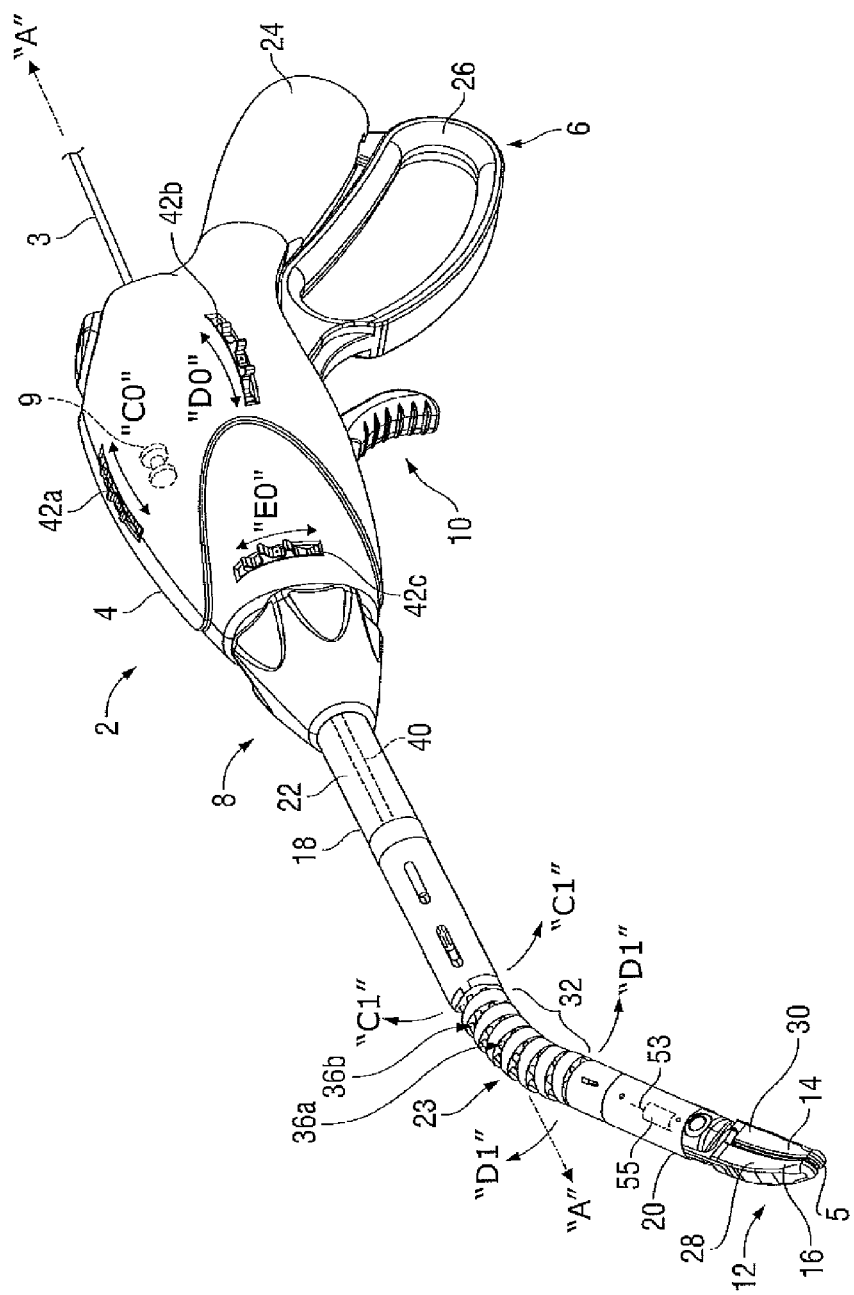
FIG. 2 is a side, perspective view of the endoscopic instrument depicted in FIG. 1 shown with the shaft in an articulated configuration.

With reference to FIGS. 1-3D, and with initial reference to FIGS. 1 and 2, an illustrative embodiment of an articulating surgical instrument, e.g., an articulating endoscopic instrument, such as, for example, an articulating endoscopic forceps 2 (forceps 2), is shown. As can be appreciated, other types of articulating instruments that are configured to treat tissue may be utilized in accordance with the present disclosure, e.g., snares, blades, loops, stabilizers, retractors, etc.

Forceps 2 is adapted to couple to an electrosurgical generator (not shown) configured for performing an electrosurgical procedure. An electrosurgical procedure may include sealing, cutting, cauterizing, coagulating, desiccating, and fulgurating tissue all of which may employ RF energy. The electrosurgical generator may be configured for monopolar and/or bipolar modes of operation. The electrosurgical generator may include or is in operative communication with one or more processors (not shown) in operative communication with the one or more control modules that are executable on the one or more processors. The control module may be configured to instruct one or more modules to transmit electrosurgical energy, which may be in the form of a wave or signal/pulse, via one or more cables (e.g., an electrosurgical cable 3) to one or both seal plates 5, 7 disposed on respective jaw housings 28 and 30. However, in certain embodiments, the forceps 2 may be battery powered.

Continuing with reference to FIGS. 1 and 2, forceps 2 is shown configured for use with various electrosurgical procedures and generally includes a housing 4, an electrosurgical cable 3 that connects the forceps 2 to an electrosurgical generator, a handle assembly 6, a rotating assembly 8, a trigger assembly 10, a drive assembly 9, and an end effector assembly 12 that operatively connects to the drive assembly 9. The drive assembly 9 may be in operative communication with handle assembly 6 for imparting movement of one or both of a pair of jaw members 14, 16 of end effector assembly 12.

With reference again to FIGS. 1 and 2, handle assembly 6 includes a fixed handle 24 and a movable handle 26. Fixed handle 24 is integrally associated with housing 4 and movable handle 26 is movable relative to fixed handle 24. Movable handle 26 of handle assembly 6 is ultimately connected to the drive assembly 9, which together mechanically cooperate to impart movement of one or both of the jaw members 14 and 16 to move from an open position (FIG. 1), wherein the jaw members 14 and 16 are disposed in spaced relation relative to one another, to a clamping or closed position, wherein the jaw members 14 and 16 cooperate to grasp tissue therebetween (FIG. 2).

Drive assembly 9 (FIGS. 1 and 2) including the drive rod 40 are in mechanical communication with the movable handle 26. More particularly, one or more gears, links, springs, or other component(s) that are operably supported and/or disposed within the housing 4 are configured to collectively provide translation of the drive rod 40 along the axis "A-A" as a result of proximal movement of the movable handle 26. Drive rod 40 may be made from any suitable material, e.g., metal. In certain embodiments, it may prove advantageous for the drive rod 40 to be relatively flexible. In this instance, the drive rod 40 may be made from a relatively flexible material, e.g., wire, band, cable, etc.

Jaw members 14, 16 are operatively and pivotably coupled to each other and located adjacent the distal end 20 of shaft 18 (FIGS. 1 and 2). For illustrative purposes, the end effector 12 is shown including a bilateral jaw configuration, i.e., both jaw members 14 and 16 are movable. However, the present disclosure contemplates that the end effector 12 may include a unilateral jaw configuration, i.e., jaw member 14 is movable with respect to jaw member 16 that is non-movable or stationary with respect to jaw member 14. Respective electrically conductive seal plates 5 and 7 are operably supported on and secured to jaw housings 28 and 30 of respective the jaw members 14 and 16. Each of the jaw members 14 and 16 is in operable communication with the drive rod 40 via the jaw operating catheter 37 (FIGS. 3A-3D) to impart movement thereof from the open configuration to the clamping configuration and vice versa.

For a more detailed description of the forceps 2 including rotating assembly 8, trigger assembly 10, and electrosurgical cable 3 (including line-feed configurations and/or connections), reference is made to commonly-owned U.S. Pat. Publication No. 2007/0173814 filed on Nov. 9, 2006.

With continued reference to FIGS. 1 and 2, housing 4 is illustrated. Housing 4 is accessible by a surgeon from outside a body cavity to control the positioning, orientation and operation of the end effector 12 when the end effector 12 is positioned inside a body cavity at a surgical site. To provide this operability, the housing 4 supports various components that are operable to induce or prohibit movement in the end effector 12 through various modes. More particularly housing 4 is configured to house or support handle assembly 6, drive assembly 9 and articulation dials 42a, 42b and a locking catheter rotation dial 42c.

Articulation dials 42a, 42b are operable to pivot the distal end 20 of an elongated shaft 18 to various articulated orientations with respect to a longitudinal axis A-A (FIGS. 1 and 2) of the shaft 18. More particularly, articulation dials 42a and 42b operably couple to a plurality of cables or tendons 34 (FIGS. 3A-3D) that are in operative communication with an articulating section 23 of the shaft 18, as described in greater detail below. Articulation dial 42a may be rotated in the direction of arrow "C0" to induce pivotal movement in a first plane, e.g., a vertical plane, as indicated by arrows "C1." Similarly, articulation dial 42b may be rotated in the direction of arrow "D0" to induce pivotal movement in a second plane, e.g., a horizontal plane, as indicated by arrows "D1." Rotation of the articulation dials 42a and 42b in either direction of arrows "C0" or "D0" results in the tendons 34 pivoting or articulating the shaft 18 about the articulating section 23.

Locking catheter rotation dial 42c (FIGS. 1 and 2) is operable to rotate a locking catheter 39 to various rotated orientations about the axis A-A defined through the shaft 18. More particularly, locking catheter rotation dial 42c may be rotated in the direction of arrow "E0" to induce rotational movement as indicated by arrow "E1," see FIG. 3A. Rotation of the locking catheter rotation dial 42c in either a clockwise or counter-clockwise direction locks the shaft 18 in one or more orientations about the articulating section 23, see FIG. 2. In one particular embodiment, rotating the locking catheter rotation dial 42c 180° in either the clockwise or counter-clockwise direction locks the shaft 18 in one or more positions about the axis "A-A."

Shaft 18 includes a generally elongated configuration and defines the axis "A-A" therethrough (FIG. 1). Shaft 18 has a distal end 20 configured to mechanically engage the end effector assembly 12 and a proximal end 22 that mechanically engages the housing 4 (FIGS. 1 and 2). Shaft 18 is defined by inner and outer walls 11 and 13 (FIGS. 3A-3D), respectively. In the embodiment illustrated in FIGS. 3A-3D, inner wall 11 of the shaft 18 includes a plurality of rings 15 that extend along a length thereof. The plurality of rings 15 is configured to engage a corresponding plurality of earn rings 43 that is operably disposed on locking ferrules 41 which is operably disposed on the tendons 34. In the embodiment illustrated in FIGS. 3A-3D, the plurality of rings 15 extend from adjacent the proximal end 22 of the shaft 18 to an articulating section 23 of the shaft 18, see FIGS. 3A-3D.

Continuing with reference to FIGS. 1 and 2, articulating portion or section 23 is operably disposed on or coupled to the shaft 18 between the proximal and distal ends 22 and 20, respectively. The articulation section 23 is defined by a plurality of links 32 (links 32) FIGS. 1-2. The links 32 are operable to articulate the shaft 18 transversely across the axis "A-A" in either the horizontal or vertical plane. For illustrative purposes, the shaft 18 is shown articulated across the horizontal plane, see FIGS. 2 and 4.

Links 32 may be made from any suitable material including, but not limited to plastics, plastic composites, ceramics, metals, and metal alloys. In the illustrated embodiment, links 32 are made from surgical steel. Links 32 are cylindrical about an outer diameter thereof and include a generally annular configuration defining a central annulus (not explicitly shown) through the articulating section 23 and are configured to receive a jaw operating catheter 37 therethrough that is configured to house a drive mechanism, e.g., a drive rod 40 (FIGS. 3A-3D), therethrough. As can be appreciated, the configuration of the central annulus provides adequate clearance for receiving jaw operating catheter 37 including the drive rod 40 (or other suitable device) therethrough. The central annulus defines a longitudinal axis "B-B" therethrough that is parallel to the axis "A-A" when the shaft 18 is in a non-articulated configuration, see FIG. 1.

Figure 3A:
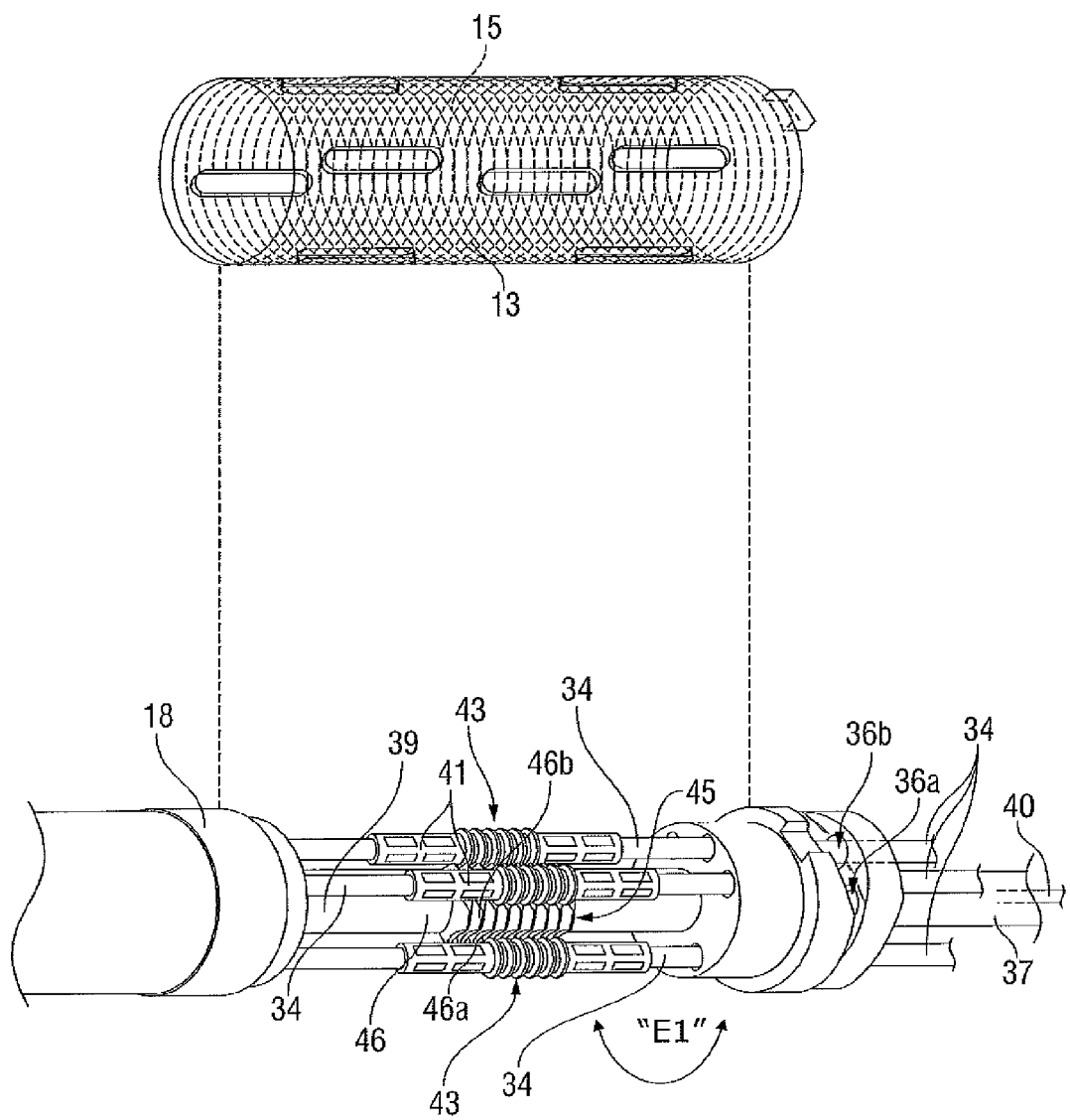
FIGS. 3A-3D are partial cut-away views of the shaft depicted in FIGS. 1 and 2 illustrating a locking catheter and locking ferrules in various locked and an unlocked configurations.

The links 32 include a corresponding plurality of first apertures or bores 36a (bores 36a) that is radially disposed along the links 32 (FIGS. 1-3) and centrally aligned along a common axis. The bores 36a are configured to receive a corresponding tendon 34 therein, as best seen in FIG. 3A. A distal-most link 32 is configured to operably couple (by suitable methods, e.g., soldering) to a distal end of each tendon of the tendons 34.

In the illustrated embodiment, the links 32 include an optional second plurality of bores 36b (bores 36b), see FIG. 1. The bores 36b are configured to function as a passage for receiving corresponding electrical wiring or other components that require communication with the jaw members 16 and 14 from the forceps 2.

The bores 36a and 36b are disposed parallel with respect to the axis "B-B" of the central annulus (FIG. 1). Moreover, the bores 36a and 36b are equally spaced-apart from each other along a radial circumference of each link 32 (FIG. 1).

With reference to FIGS. 3A-3D, tendons 34 operably couple the links 32 to articulation dials 42a and 42b. For illustrative purposes, 3 (3) tendons 34 are shown (FIG. 3A). The articulating dials 42a and 42b are configured to actuate the tendons 34, i.e., "pull" one of an opposed pair of the tendons 34 proximally when one of the articulating dials 42a, 42b is rotated, and permit the other of the opposed pair of tendons 34 to translate distally. In particular, the tendons 34 are translatable under the same tension along the longitudinal axis "A-A" when respective articulation dial 42a and 42b is rotated. The tendons 34 may be constructed of stainless steel wire or other material suitable for transmitting tensile forces to a distal-most link of the links 32. Regardless of the construction materials, the tendons 34 exhibit a spring rate that is amplified over the length of the tendons 34 and thus, the tendons 34 may tend to stretch when external loads are applied to the elongated shaft 18. This tendency to stretch may be associated with an unintended change in orientation of the distal portion 22 of the elongated shaft 18, e.g., without a corresponding movement of the articulation dials 42a, 42b initiated by the surgeon.

Continuing with reference with FIGS. 3A-3D, each tendon of the tendons 34 includes a respective locking ferrule 41 (hereinafter collectively referred to as ferrules 41) operably coupled thereto by suitable coupling methods. In the illustrated embodiments, the ferrules 41 are coupled to a respective tendon 34 via crimping. Ferrules 41 may include any suitable shape and may be made from any suitable material including, but not limited to the previously described materials. In the illustrated embodiments, ferrules 41 include a generally tubular configuration and are made from a substantially rigid plastic.

Ferrules 41 are configured to move or translate with the tendons 34 along the longitudinal axis "A-A" when the rotation dials 42a and 42b are rotated and are configured to selectively engage a locking catheter 39. To this end, and in the embodiment illustrated in FIGS. 3A-3D, ferrules 41 include an outer surface having a plurality of cam rings 43 (cam rings 43) disposed therealong. The cam rings 43 may be spaced-apart from one another at predetermined positions along the outer surface of the ferrules 41. The cam rings 43 are configured to selectively contact or engage the locking catheter 39 (see FIGS. 3B and 3D) when the locking catheter 39 is rotated to a locking position, as described in greater detail below.

Figure 3B:
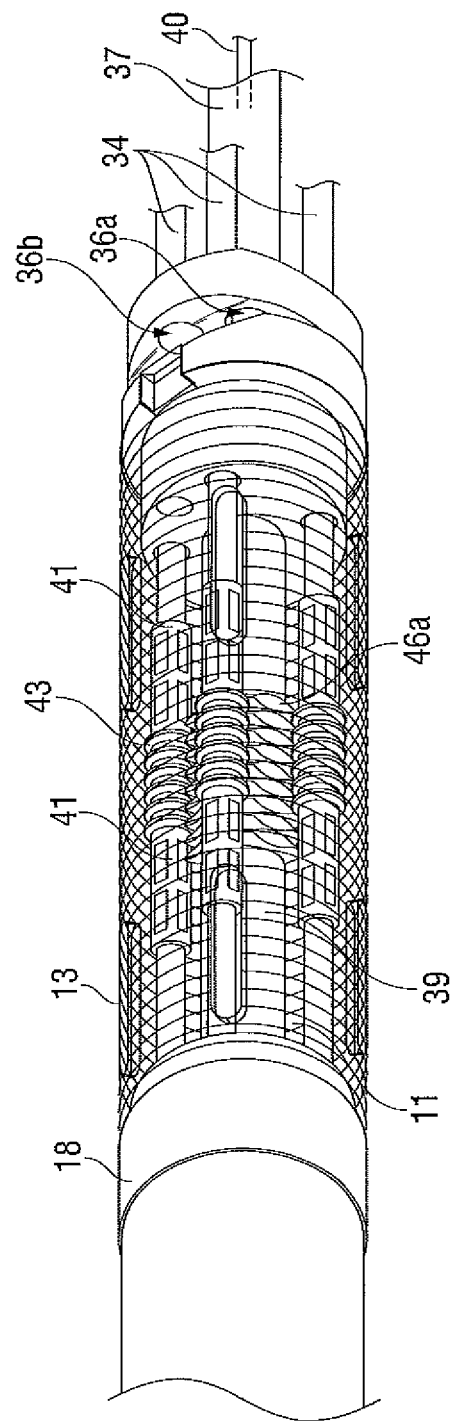
Figure 3C:
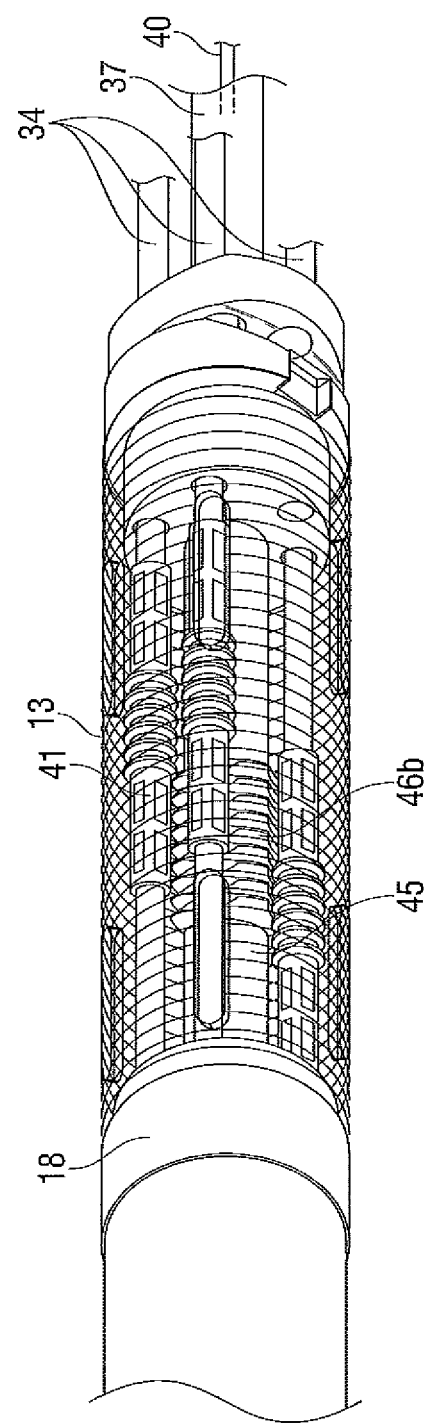
Figure 3D:
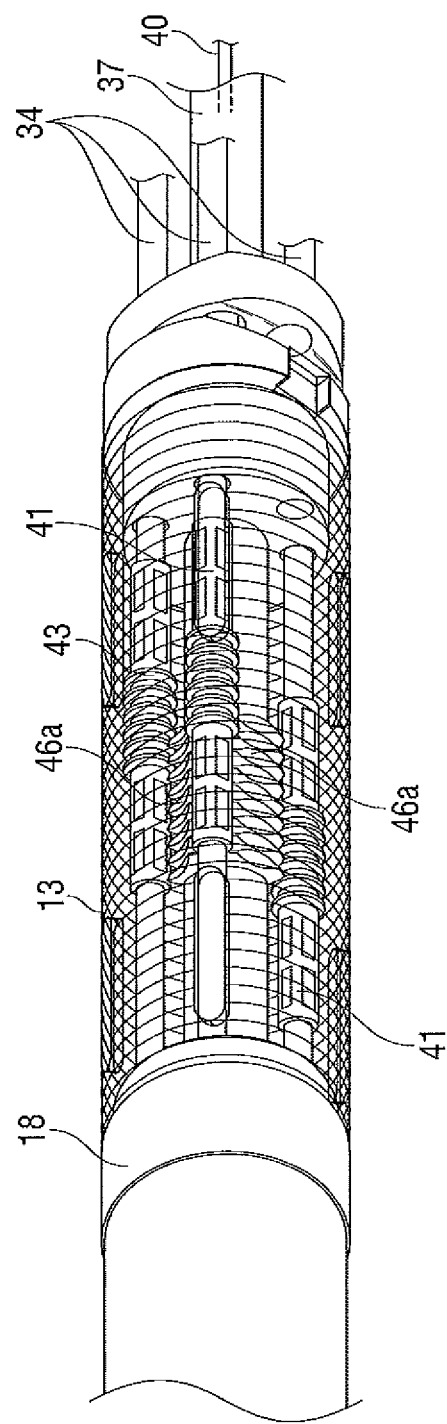

With continued reference to FIGS. 3A-3D, locking catheter 39 is illustrated including a generally elongated configuration. Locking catheter 39 is disposed within the shaft 18 and between the tendons 34, see FIGS. 3A-3D. Locking catheter 39 is configured to selectively engage one or more of the ferrules 41. To this end, the locking catheter 39 is rotatable within the shaft 18. In particular, the locking catheter 39 is rotatable from a first position, wherein the locking catheter 39 is disengaged from the ferrules 41 (FIGS. 3A and 3C), to a second position, wherein the locking catheter 39 is engaged with the ferrules 41. In the first (or disengaged position) the locking catheter 39 is configured to allow axial movement of the tendons 34 including the ferrules 41 along the longitudinal axis "A-A" (FIGS. 3A and 3C) such that the shaft 18 may be articulated about the articulating section 23 (FIGS. 2, 3C and 3D). In the second (or engaged position) the locking catheter 39 is configured to prevent axial movement of the tendons 34 including the ferrule 41 along the longitudinal axis "A-A" (FIGS. 3B and 3D) to lock the shaft 18 in one or more positions with respect to the longitudinal axis "A-A" (FIGS. 2, 3C and 3D).

In the embodiment illustrated in FIGS. 3A-3D, the locking catheter 39 includes a camming surface 45 that is radially displaced from an outer surface of the locking catheter 39. The camming surface 45 is segmentally relieved to match the cam pattern of the tendons 34. That is, in the first position, the segmentally-relieved portion of camming surface 45 is not configured to contact or engage the ferrules 41; this facilitates axial movement of the tendons 34 including the ferrules 41 along the longitudinal axis "A-A" and articulation of the shaft 18 about the articulating section 23. In the second position, the camming surface 45 causes an outward, radial displacement of the ferrules 41 such that the ferrules 41 come into contact with, i.e., mesh or engage, the rings 15 on inner wall 13 of the shaft 18. This contact between the ferrules 41 and the inner wall 13 prevents axial movement of the tendons 34 including the ferrules 41 along the longitudinal axis "A-A" and articulation of the shaft 18 about the articulating section.

In the embodiment illustrated in FIGS. 3A-3D, the camming surface 45 is defined by a plurality of segmentally-relieved rings 46 (relieved rings 46) that extend along a length of the locking catheter 39. The relieved rings 46 are configured to correspond to the tendons 34 in such a way that in the first position, a relieved portion 46a (FIGS. 3A-3C) of the relieved rings 46 are aligned with the ferrules 41 and, in the second position, a ringed portion 46b (FIGS. 3A and 3C) of the relieved rings 46 contact or engage the ferrules 41 and cam the ferrules 41 against the rings 15 on inner wall 13 of the shaft 18. As a result of the ringed portion 46b camming the ferrules 41 against the rings 15, the tendons 34 are prevented from moving along the longitudinal axis "A-A," which, in turn, locks the shaft 18 in one or more positions with respect to the longitudinal axis "A-A," FIGS. 3B and 3D. In the illustrated embodiments, the relieved rings 46 include four (4) relieved portions 46a and four ringed portions 46b. Each of the relieved portions 46a are spaced-apart approximately 90° from each other. Similarly, each of the ringed portions 46b are spaced-apart approximately 90° from each other. As can be appreciated, the specific spacing configuration of the relieved portion 46a and/or ringed portion 46b may be adjusted as needed during the manufacturing process to accommodate a specific surgical procedure, a specific manufacturer's preference, a specific locking catheter 39, etc.

Jaw operating catheter 37 (FIGS. 3A-3D) includes a generally tubular configuration and may be made from any of the aforementioned materials described above with respect to links 32. In the illustrated embodiments, jaw operating catheter 37 is made from a relatively elastic material to facilitate articulating the shaft 18 about the articulating section 23. Jaw operating catheter 37 is configured to house the driving structure, e.g., drive rod 40 (FIG. 1), therethrough to move one or both of the jaw members 14 and 16 from the open configuration (FIG. 1) to the clamping configuration (FIG. 2). The jaw operating catheter 37 may be configured to house a drive wire (not explicitly shown) that is operably coupled to a cutting element (not explicitly shown) that is in operable communication with the jaw members 14 and 16. The drive wire may be translatable within the jaw operating catheter 37 to translate the cutting element longitudinally through one or both of jaw members 14 and 16.

In use, jaw members 14 and 16, initially, are in open position (FIG. 1) and the locking catheter 39 is in an unlocked configuration (FIG. 3A). That is, the locking catheter 39 is in an initial, disengaged configuration. To position the jaw members 14 and 16 adjacent target tissue, one or both of the articulation dials 42a and 42b may be rotated to articulate the shaft 18 about articulating section 23, i.e., transversely across the axis "A-A" (FIG. 2).

To lock the shaft 18 in the articulated configuration, the locking catheter rotation dial 42c may be rotated, e.g., approximately 45° in either the clockwise or counter clockwise direction. As locking catheter 39 rotates, ringed portions 46b thereon contact or engage the cams rings 43 on the ferrules 41 and press the cam rings 43 against the rings 15 on the inner wall 11 of the shaft 18 (FIGS. 3B and 3D). As can be appreciated, with the cam rings 43 pressing or leaning against the rings 15, the tendons 34 are prevented from moving, which, in turn, prevents the shaft 18 from articulating about the articulating section 23.

When the tendons 34 are in the locked configuration (FIGS. 2, 3B and 3D) the tendons 34 are in a loaded state, but not under high tension as is typically the case with conventional shafts that are configured to articulate. That is, the tendons 34 are loaded only at specific locations therealong, i.e., at locations adjacent the ferrules 41, and not along a substantial length of the tendons 34. As can be appreciated, the tendons 34 retain their ability to stretch and the stiffness of the shaft 18 is not compromised.

To unlock or articulate the shaft 18, the locking catheter rotation dial 42c may be rotated approximately 45° in a direction opposite to the direction rotated to lock the shaft 18 to return the locking catheter 39 back to its initial, disengaged configuration, which, in turn, moves the ringed portion 46b back to the initial unlocked configuration, i.e., the relieved portion 46a of the relieved rings 46 are aligned with the ferrules 41, see FIGS. 3A and 3C. Alternatively, the locking catheter rotation dial 42c may be rotated approximately an additional 45° in the same direction as rotated to lock the shaft 18 to move the locking catheter to 39 to a disengaged configuration.

With reference to FIGS. 4A-4D, an alternate embodiment of the locking catheter 39 and ferrules 41 that is configured for use with the forceps 2 is illustrated. In this embodiment, ferrules 141, locking catheter 139 and inner wall 111 of a shaft 118 are configured to function similar to that of ferrules 41, locking catheter 39 and inner wall 11 of the shaft 18. In view thereof, only those features unique to the ferrules 141, locking catheter 139 and inner wall 111 of shaft 118 are described in detail.

Figure 4A:
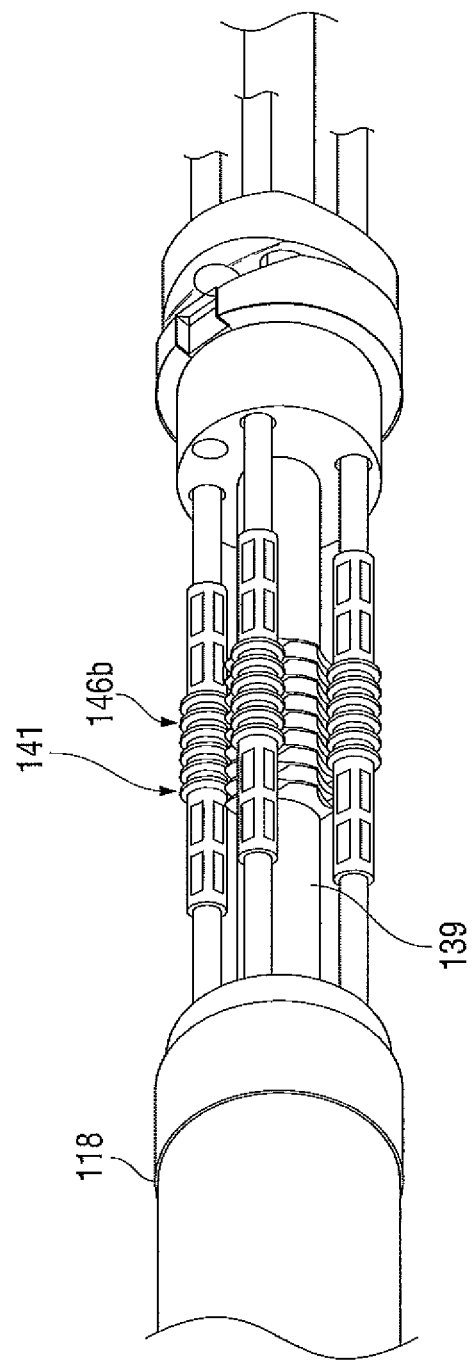
FIGS. 4A-4D are partial cut-away views of a shaft illustrating a locking catheter and locking ferrules in various locked and an unlocked configurations according to another embodiment of the present disclosure.
Figure 4B:
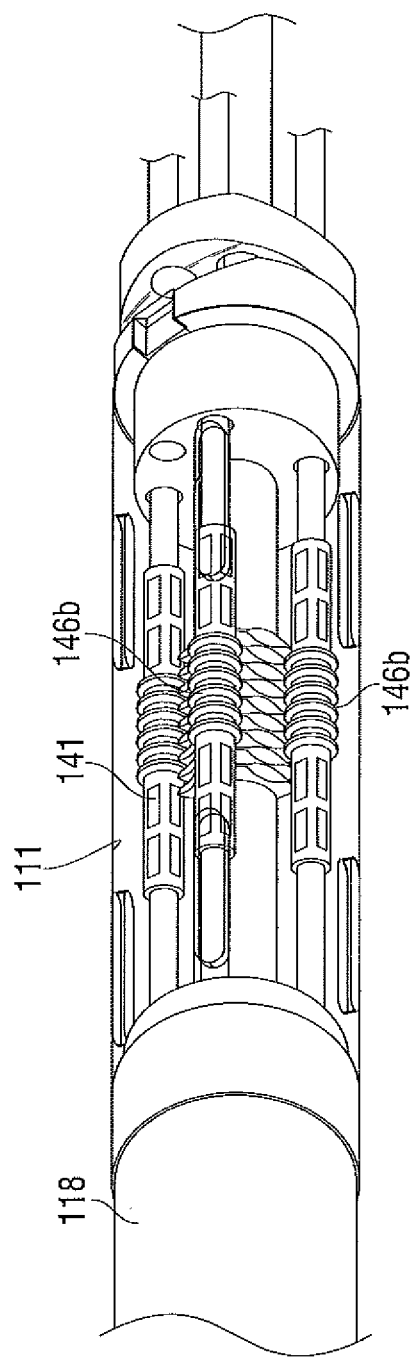
Figure 4C:
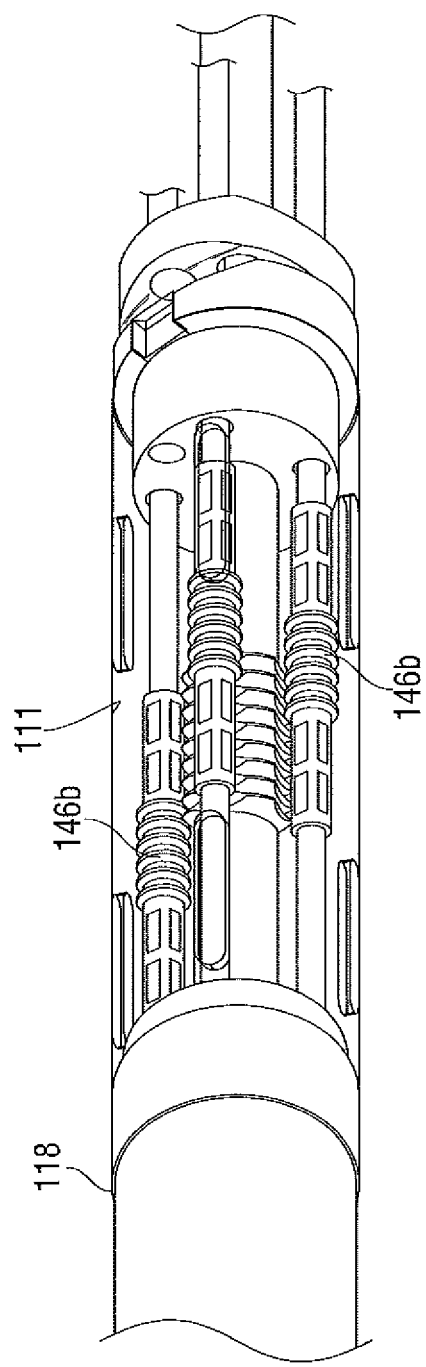
Figure 4D:
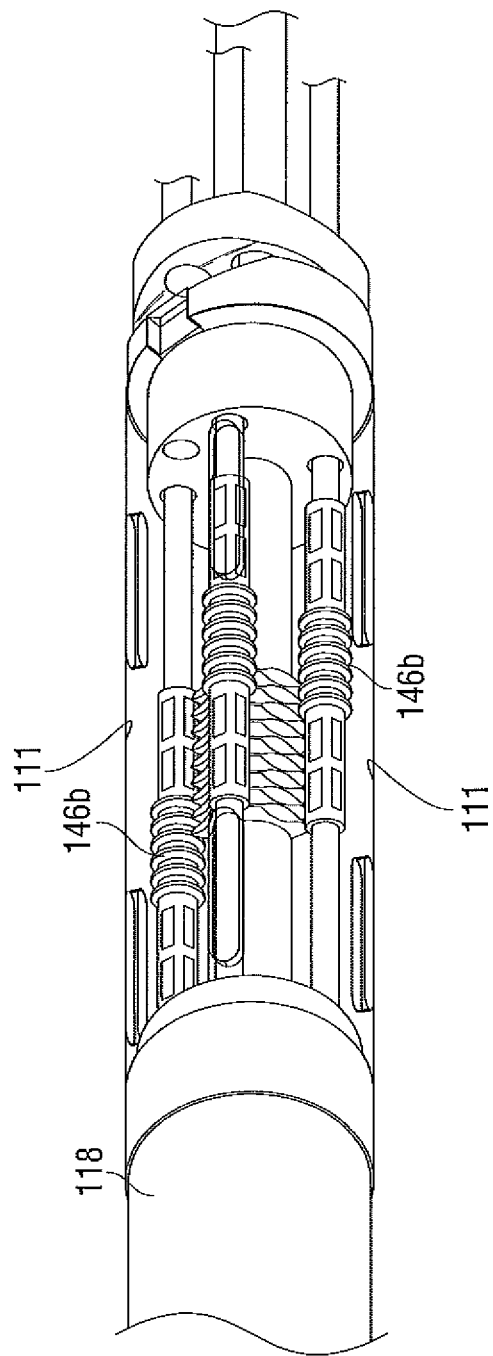

Unlike shaft 18, shaft 118 includes a smooth inner wall 111 (FIGS. 4B-4D). Accordingly, in this instance, the locking catheter 139 is not configured to engage the inner wall 111. This embodiment is particularly useful in the instance where a plurality of leads or other internal structure of the shaft 118 need to be feed therethrough. In addition, the shaft 118 with a smooth inner wall 111 offers an infinite number of locking positions rather than discrete segments, and is cheaper and easier to manufacture.

Operation of the forceps 2 with the locking catheter 139 and ferrules 141 is substantially similar to that of the forceps 2 with the locking catheter 39 and ferrules 41. Unlike ferrules 41, however, a ringed portion 146b of the ferrules 141 is not configured to engage or otherwise contact the inner wall 111 of the shaft 118 when the locking catheter is in an engaged configuration, see FIGS. 4B and 4D. Incidental or smooth frictional contact is possible between the ferrules 141 and the inner wall 111 without positive engagement therebetween.

With reference to FIGS. 5A-5D, an alternate embodiment of the locking catheter 39 and ferrules 41 that is configured for use with the forceps 2 is illustrated. In this embodiment, ferrules 241, a locking catheter 239 and an inner wall 211 of a shaft 218 are configured to function similar to as hereinbefore described. In view thereof, only those features unique to the ferrules 241, locking catheter 239 and inner wall 211 of shaft 218 are described in detail.

Similar to that of shaft 118, shaft 218 includes a smooth inner wall 211. Unlike the previously described locking catheters, e.g., locking catheter 39, locking catheter 239 includes a camming surface 245 defined by a plurality of segmentally relieved threads 246 (threads 246) that extend along a length of the locking catheter 239. The threads 246 are configured to correspond to the tendons 234 in such a way that in the first position, a relieved portion 246a of the threads 246 are aligned with the ferrules 241 and, in the second position, a threaded portion 246b of the threads 246 contact or engage the ferrules 241.

Operation of the forceps 2 with the locking catheter 239 and ferrules 241 is substantially similar to that of the forceps 2 with the locking catheter 139 and ferrules 141.

In particular, to lock the shaft 218 in the articulated configuration, the locking catheter rotation dial 42c may be rotated, e.g., approximately 45° in either the clockwise or counter clockwise direction. As locking catheter 239 rotates, threaded portions 246b thereon contact or engage the cams rings 243 on the ferrules 241 and, in some instances, press the cam rings 243 against the inner wall 211 of the shaft 218 (FIGS. 513 and 5D). As can be appreciated, with the cam rings 243 engaged with the threaded portions 246b, the tendons 234 are prevented from moving, which, in turn, prevents the shaft 218 from articulating about the articulating section 23.

Figure 5A:
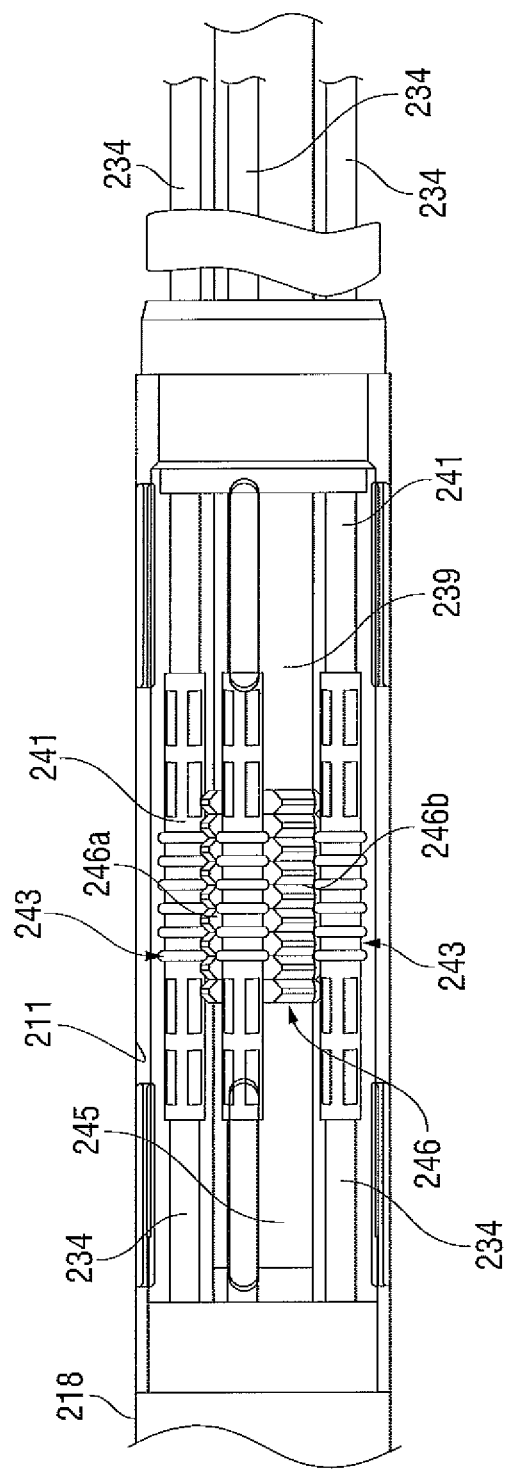
FIGS. 5A-5D are partial cut-away views of a shaft illustrating a locking catheter and locking ferrules in various locked and an unlocked configurations according to still another embodiment of the present disclosure.
Figure 5B:
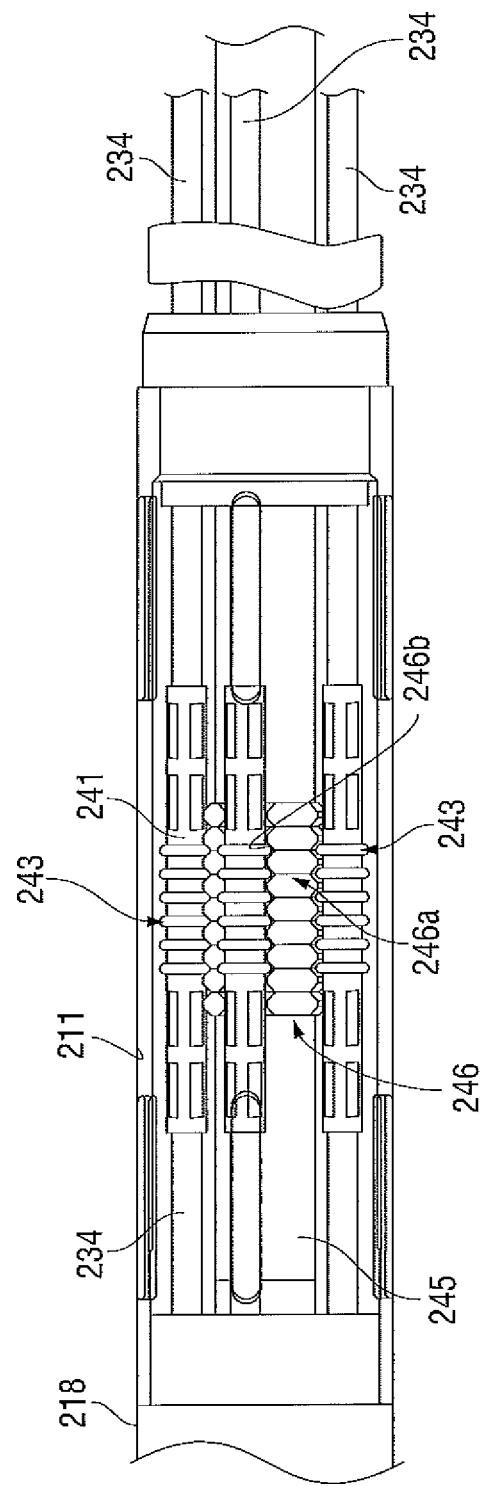
Figure 5C:
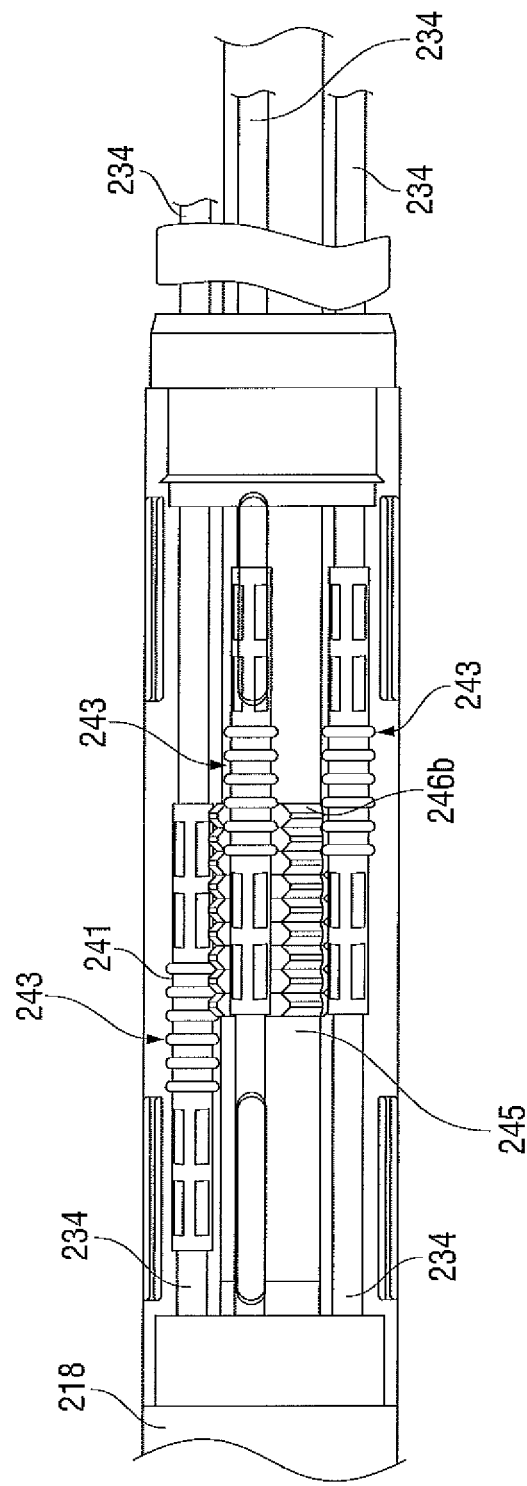
Figure 5D:
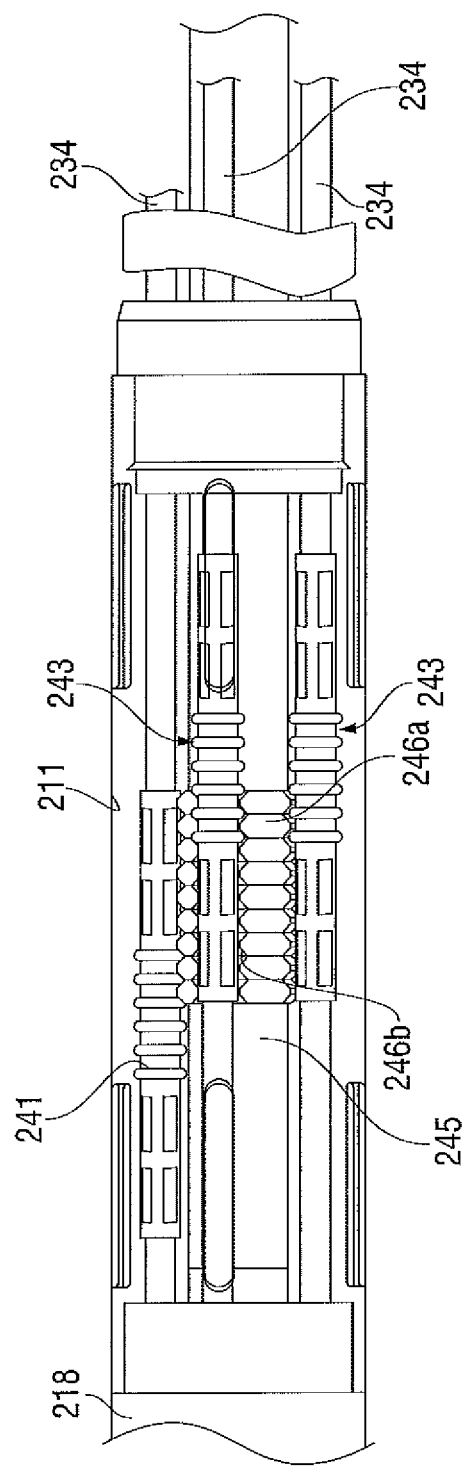
Figure 6A:
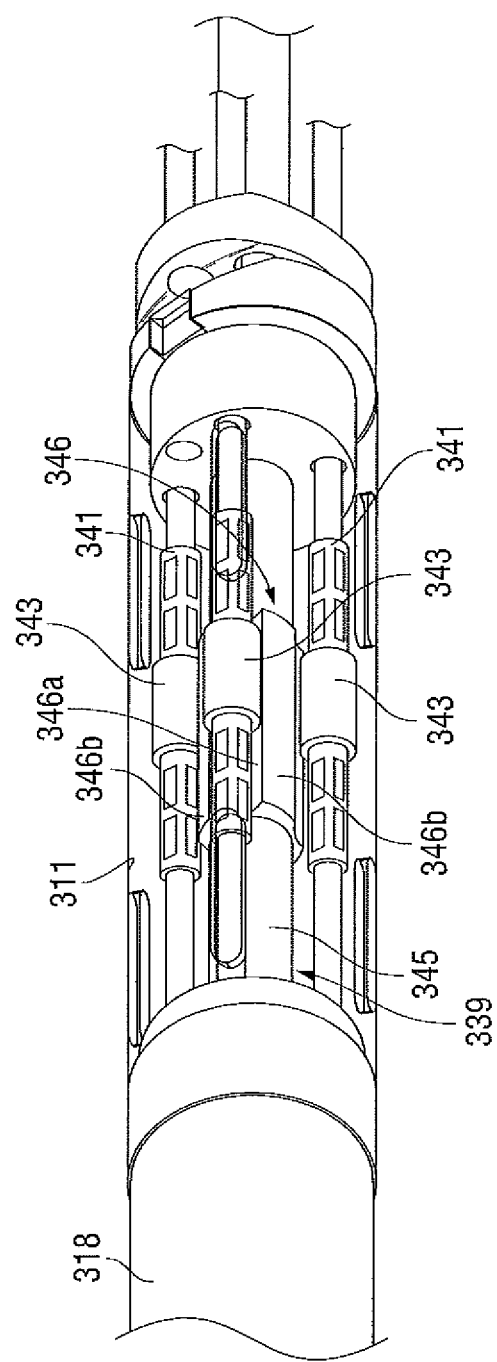
Figure 6B:
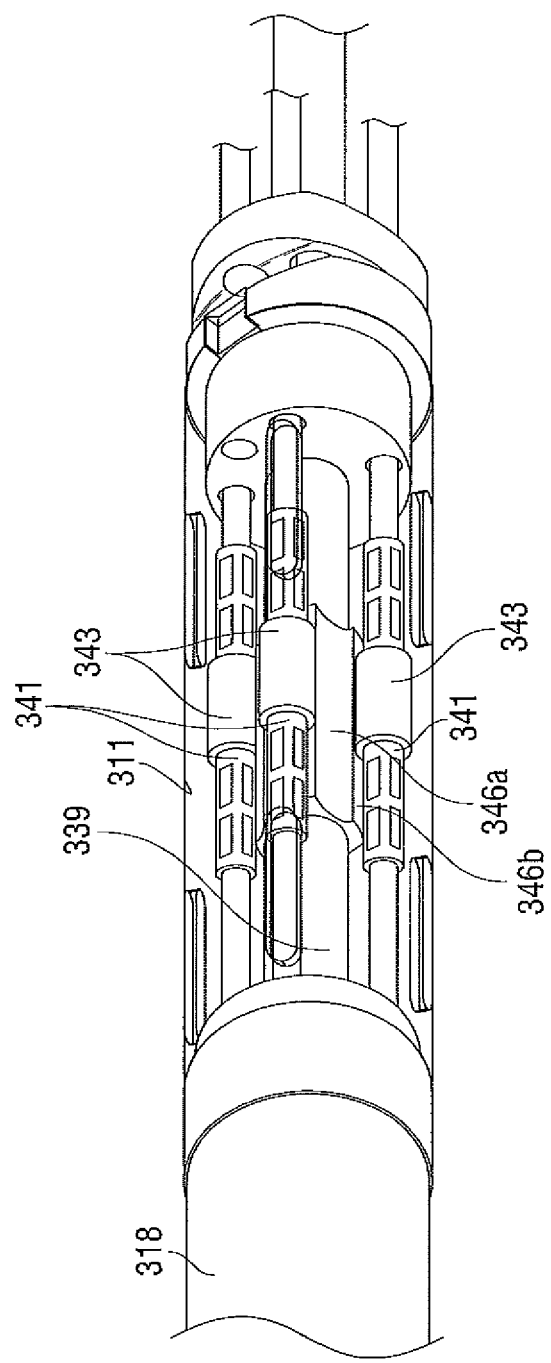
Figure 6C:
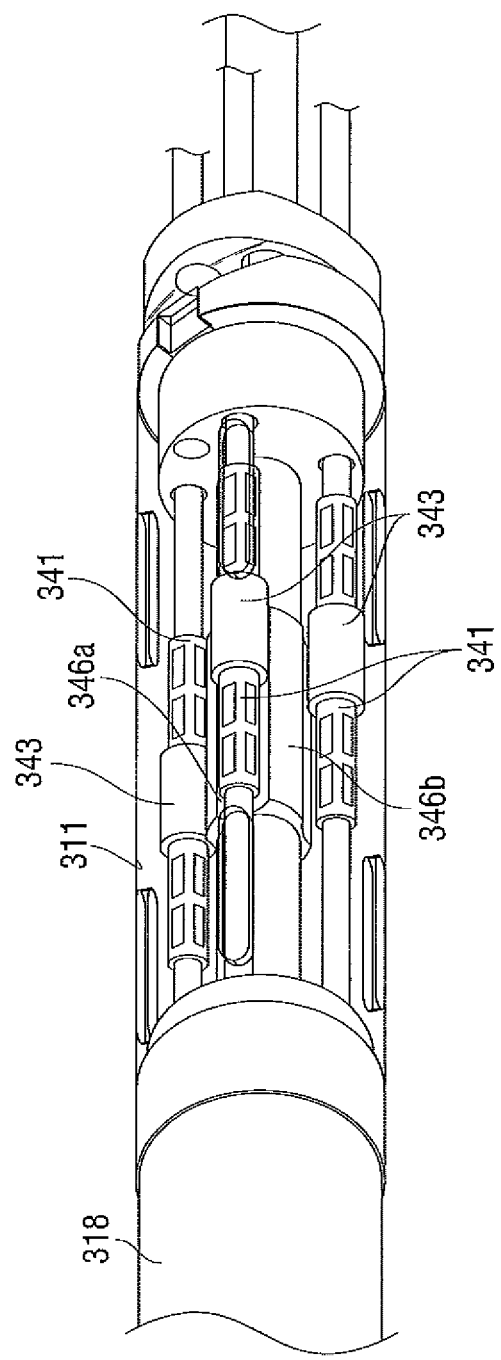
Figure 7A:
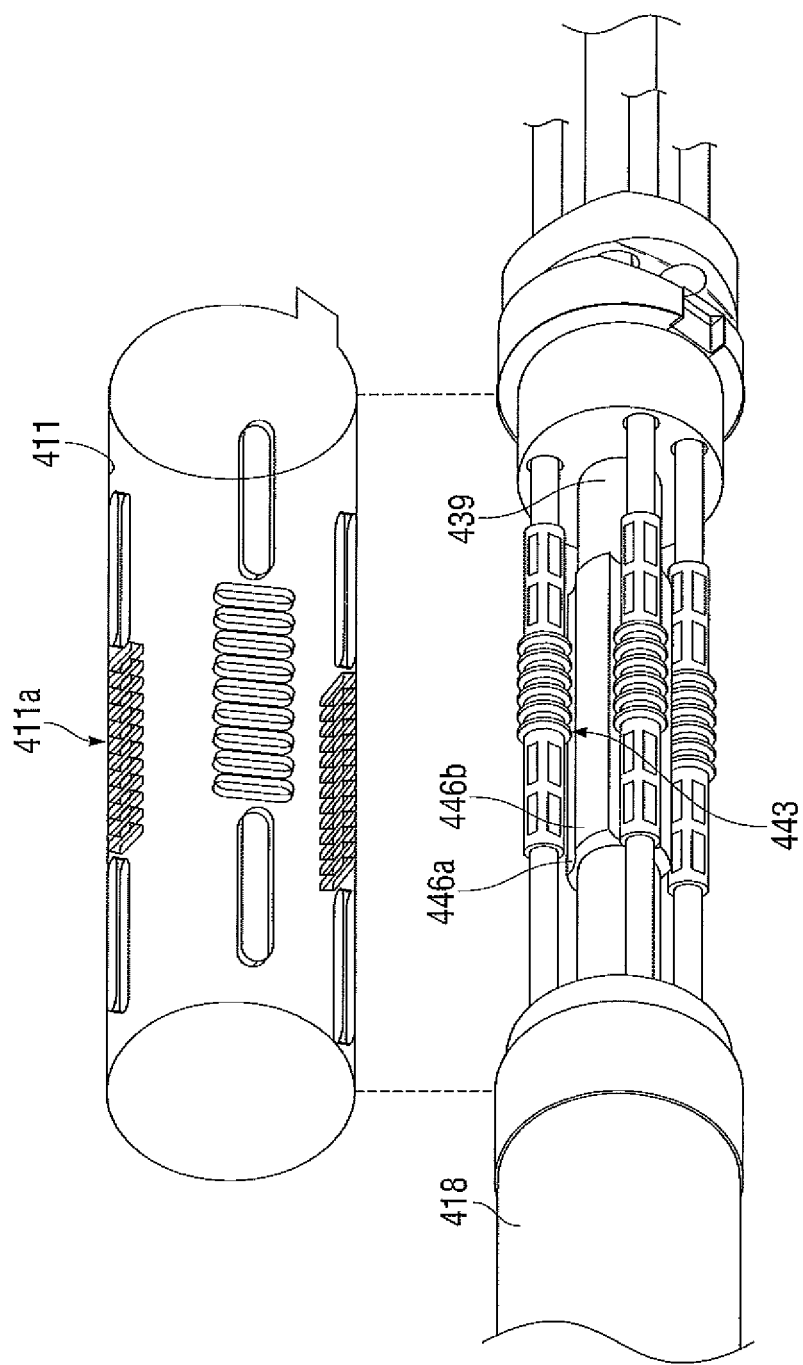
FIGS. 7A-7D are partial cut-away views of a shaft illustrating a locking catheter and locking ferrules in various locked and an unlocked configurations according to still yet another embodiment of the present disclosure.
Figure 7B:
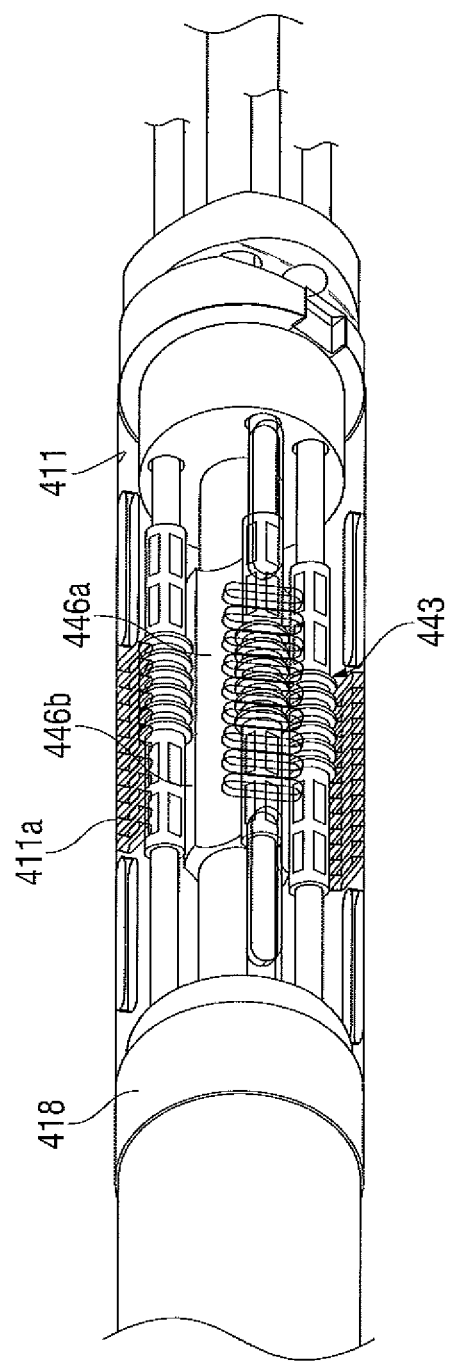
Figure 7C:
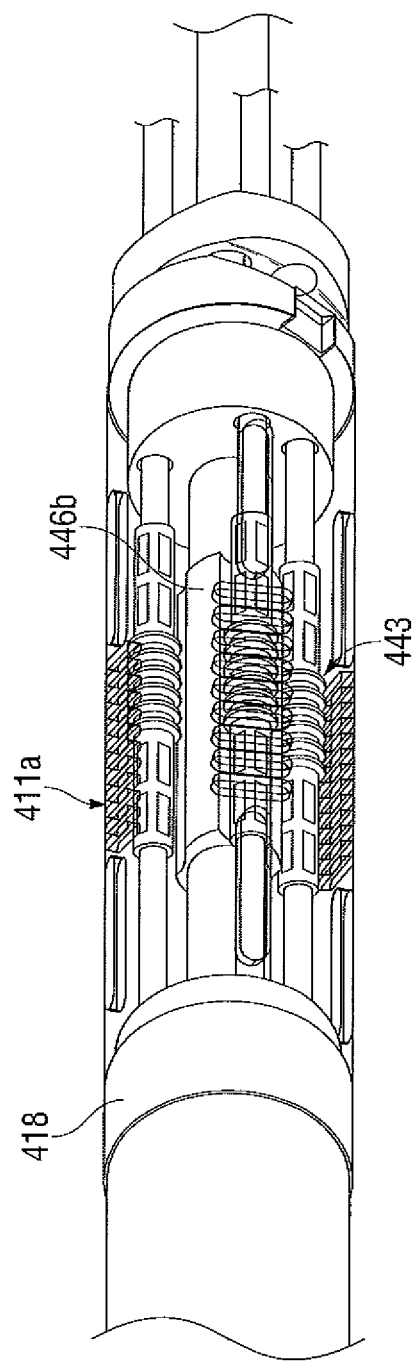
Figure 7D:
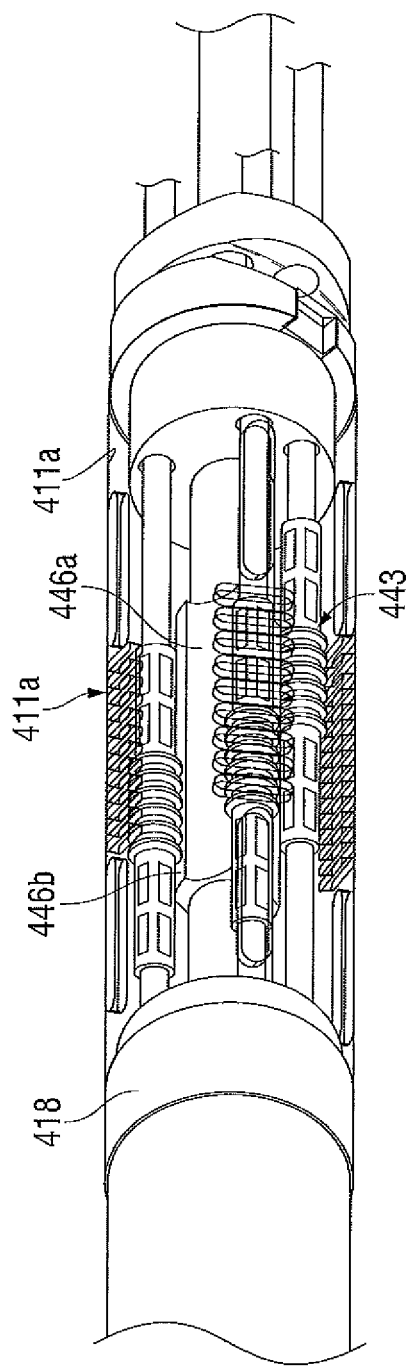

To unlock or articulate the shaft 218, the locking catheter rotation dial 42c may be rotated approximately 45° in a direction opposite to the direction as rotated to lock the shaft 218 to return the locking catheter 239 back to its initial, disengaged configuration, which, in turn, moves the threaded portion 246b back to the initial unlocked configuration, i.e., the relieved portion 246a of the threads 246 are aligned with the ferrules 241, see FIGS. 5A and 5C. Alternatively, the locking catheter rotation dial 42c may be rotated approximately an additional 45° in the same direction as rotated to lock the shaft 218 to move the locking catheter 239 to a disengaged configuration.

With reference to FIGS. 6A-6D, an alternate embodiment of the locking catheter 39 and ferrules 41 that is configured for use with the forceps 2 is illustrated. In this embodiment, ferrules 341, locking catheter 339 and an inner wall 311 of a shaft 318 are configured to function similar to that of ferrules 41, locking catheter 39 and an inner wall 11 of a shaft 18. Unlike the previously described locking catheters, e.g., locking catheter 39, locking catheter 339 includes a camming surface 345 having a plurality of longitudinal spaced-apart detents 346b (detents 346b) that extend along a length thereof, see FIGS. 6A-6D. Between each of the detents 346b is a generally arcuate indent 346a of suitable configuration (FIGS. 6A-6D). The configuration of the detents 346b and indents 346a matches the tendons 334 to facilitate axial movement the tendons 334 including the respective locking ferrules 341 (ferrules 341) along the longitudinal axis "A-A." In the embodiment illustrated in FIGS. 6A-6D, the detents 346b and indents 346b may be spaced-apart along the locking catheter 339 in a manner consistent with that of the ringed portion 46b and relieved portion 46a described above.

Unlike the previously described ferrules, ferrules 341 include a relatively smooth cam member 343 that is configured to engage the detents 346 of the locking catheter 339.

Operation of the forceps 2 with the locking catheter 339 and ferrules 341 is substantially similar to that of the forceps 2 with the locking catheter 139 and ferrules 141. However, unlike the previously described locking catheters, e.g., locking catheter 39, and ferrules, e.g., ferrules 41, that may mesh with one another when the locking catheter 39 is in a locked configuration, the detents 346 and the camming member 343 do not mesh with one another, but instead press against one another to create a frictional interface therebetween, see FIGS. 6B and 6D.

With reference to FIGS. 7A-7D, an alternate embodiment of the locking catheter 39 and ferrules 41 that is configured for use with the forceps 2 is illustrated. In this embodiment, ferrules 441, locking catheter 439 and an inner wall 411 of a shaft 418 are configured to function similar to that of ferrules 41, locking catheter 39 and an inner wall 11 of a shaft 18. Locking catheter 439 includes the detents 446b (detents 446b) and the indents 446a. Ferrules 441 include rings 443. And, unlike inner wall 11, inner wall 411 includes a notched area 411a that is disposed along predetermined locations along the inner wall 411. Notched area 415 is configured to engage or mesh with the rings 441 in a manner similar to that of rings 15 described above, see FIGS. 7B and 7D.

To lock the shaft 418 in the articulated configuration, the locking catheter rotation dial 42c is rotated as described hereinbefore. As locking catheter 439 rotates, detents 446a disposed thereon contact or engage the rings 443 on the ferrules 441 and press the cam rings 443 against notched area 415 on the inner wall 411 of the shaft 418 (FIGS. 7B and 7D), which, in turn, prevents the shaft 418 from articulating.

From the foregoing and with reference to the various figure drawings, those skilled in the art will appreciate that certain modifications can also be made to the present disclosure without departing from the scope of the same. For example, in certain instances, to simplify manufacture of the shaft 18, it may prove advantageous to have a shaft with an articulating portion that includes a compliant cylindrical extrusion. In this instance, the entire shaft 18 may be made from a compliant extrusion. An interior of the shaft 18 may include apertures or lumens that are formed during the extrusion process of the shaft 18. The lumens take the place of the first and second plurality of bores 36a and 3b. To this end, the lumens may extend along a length of the shaft 18 such that a desired amount of articulation may be achieved.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:
1. An endoscopic instrument, comprising:
a housing having a shaft extending therefrom that defines a longitudinal axis therethrough, the shaft including an articulating section disposed thereon;
an end effector assembly operatively connected to a distal end of the shaft and configured to treat tissue;

a plurality of tendons operably coupled to the articulating section, each tendon of the plurality of tendons translatable along the longitudinal axis to effect articulation of the shaft about the articulating section thereof, each tendon of the plurality of tendons including a respective locking ferrule disposed thereon; and a generally elongated locking catheter disposed within the shaft and between the plurality of tendons configured to selectively engage the locking ferrules, the locking catheter rotatable within the shaft and with respect to the shaft from a first angular position, wherein the locking catheter is disengaged from the locking ferrules to allow axial movement of the plurality of tendons including along the longitudinal axis to articulate the shaft, to a second angular position, wherein the locking catheter is engaged with the locking ferrules to prevent axial movement of the plurality of tendons along the longitudinal axis and prevent further articulation of the shaft; and a camming surface is radially displaced about an outer surface of the locking catheter, the camming surface segmentally relieved along an outer surface thereof to facilitate axial movement of the plurality of tendons including the respective locking ferrules along the longitudinal axis.

2. An endoscopic instrument according to claim 1, wherein the plurality of tendons is defined by four tendons.

3. An endoscopic instrument according to claim 1, wherein the locking catheter rotates approximately 45° when moved from the first angular position to the second angular position and vice versa such that in the first position each locking ferrule is positioned within a relieved portion of the camming surface and in the second position each locking ferrule is contacts the camming surface of the locking catheter.

4. An endoscopic instrument according to claim 1, wherein in the second position the camming surface of the locking catheter engages each respective locking ferrule to prevent axial movement of the plurality of tendons and further articulation of the shaft.

5. An endoscopic instrument according to claim 4, wherein the camming surface of the locking catheter is defined by a plurality of segmentally-relieved rings that extend along a length thereof, the rings configured in a first position to engage corresponding rings disposed on an outer surface of the locking ferrule to prevent axial movement of the tendons and configured in a second position to facilitate axial movement of the ferrules to articulate the shaft.

6. An endoscopic instrument according to claim 4, wherein the camming surface of the locking catheter is defined by a plurality of segmentally-relieved threads that extend along a length thereof, the threads configured in a first position to engage corresponding rings disposed on an outer surface of the locking ferrule to prevent axial movement of the tendons and configured in a second position to facilitate axial movement of the ferrules to articulate the shaft.

7. An endoscopic instrument according to claim 4, wherein the camming surface of the locking catheter is defined by a plurality of longitudinal spaced-apart detents that extend along a length thereof, the detents configured in a first position to engage corresponding detents disposed on an outer surface of the locking ferrule to prevent axial movement of the tendons and configured in a second position to facilitate axial movement of the ferrules to articulate the shaft.

8. An endoscopic instrument according to claim 4, wherein the camming surface of the locking catheter is defined by a plurality of longitudinal spaced-apart detents that extend along a length thereof, the longitudinal spaced-apart detents configured in a first position to engage corresponding rings disposed on an outer surface of the locking ferrule to prevent axial movement of the tendons and configured in a second position to facilitate axial movement of the ferrules to articulate the shaft.

9. An endoscopic instrument according to claim 1, wherein each respective locking ferrule is coupled to each tendon of the plurality of tendons via crimping.

10. An endoscopic instrument according to claim 1, wherein the locking catheter is operably coupled to a locking dial coupled to the housing and configured to rotate the locking catheter from the first position to the second position and vise versa.

11. An endoscopic instrument, comprising:
a housing having a shaft extending therefrom that defines a longitudinal axis therethrough, the shaft having inner and outer walls and including an articulating section disposed thereon;

an end effector assembly operatively connected to a distal end of the shaft and configured to treat tissue members;

a plurality of tendons operably coupled to the articulation section, each tendon of the plurality of tendons translatable along the longitudinal axis to effect articulation of the shaft about the articulating section thereof, each tendon of the plurality of tendons including a respective locking ferrule disposed thereon; and a generally elongated locking catheter disposed within the shaft and between the plurality of tendons configured to selectively engage the locking ferrules, the locking catheter rotatable within the shaft and with respect to the shaft from a disengaged angular position to allow articulation of the shaft about the articulating section, to an engaged angular position, wherein the locking catheter cams the locking ferrules against the inner wall of the shaft to prevent axial movement thereof along the longitudinal axis and further articulation of the shaft; and a camming surface is radially displaced about an outer surface of the locking catheter, the camming surface segmentally-relieved along an outer surface thereof to facilitate axial movement of the plurality of tendons including the respective locking ferrules along the longitudinal axis.

12. An endoscopic instrument according to claim 11, wherein the camming surface of the locking catheter is further defined by a plurality of segmentally relieved rings that extend along a length thereof, wherein the plurality of segmentally relieved rings is configured to match the plurality of tendons to facilitate axial movement the plurality of tendons including the respective locking ferrules along the longitudinal axis.

13. An endoscopic instrument according to claim 11, wherein the camming surface of the locking catheter is defined by a plurality of segmentally-relieved rings that extend along a length thereof, the rings configured in a first position to engage corresponding rings disposed on an outer surface of the locking ferrule to prevent axial movement of the tendons and configured in a second position to facilitate axial movement of the ferrules to articulate the shaft.

14. An endoscopic instrument according to claim 11, wherein the camming surface of the locking catheter is defined by a plurality of segmentally-relieved threads that extend along a length thereof, the threads configured in a first position to engage corresponding rings disposed on an outer surface of the locking ferrule to prevent axial movement of the tendons and configured in a second position to facilitate axial movement of the ferrules to articulate the shaft.

15. An endoscopic instrument according to claim 11, wherein the camming surface of the locking catheter is defined by a plurality of longitudinal spaced-apart detents that extend along a length thereof, the detents configured in a first position to engage corresponding detents disposed on an outer surface of the locking ferrule to prevent axial movement of the tendons and configured in a second position to facilitate axial movement of the ferrules to articulate the shaft.

16. An endoscopic instrument according to claim 11, wherein the camming surface of the locking catheter is defined by a plurality of longitudinal spaced-apart detents that extend along a length thereof, the longitudinal spaced-apart detents configured in a first position to engage corresponding rings disposed on an outer surface of the locking ferrule to prevent axial movement of the tendons and configured in a second position to facilitate axial movement of the ferrules to articulate the shaft.

\* \* \* \* \*